United States Patent [19]

Watanabe et al.

[11] Patent Number: 4,589,771

[45] Date of Patent: May 20, 1986

[54] ELECTRO-OPTICAL LIQUID DETECTOR ASSEMBLY

[75] Inventors: Takashi Watanabe, Kariya; Yoshihiro Sasage, Hamana, both of Japan

[73] Assignee: Nippondenso Co., Ltd., Kariya, Japan

[21] Appl. No.: 623,561

[22] Filed: Jun. 22, 1984

[30] Foreign Application Priority Data

Jun. 28, 1983 [JP] Japan .................... 58-116456

[51] Int. Cl.[4] ........................... G01N 21/00
[52] U.S. Cl. ................... 356/38; 15/250 C; 318/483; 318/DIG. 2
[58] Field of Search .......... 356/37, 38, 136, 239, 356/240; 250/564, 573, 574; 73/29; 318/444, 483, DIG. 2; 15/250 C

[56] References Cited

U.S. PATENT DOCUMENTS 4,355,271 10/1982 Noack .................. 318/483 X
4,481,450 11/1984 Watanabe et al. .......... 318/444

FOREIGN PATENT DOCUMENTS 89250 5/1984 Japan ................. 15/250 C

Primary Examiner—Davis L. Willis
Assistant Examiner—Matthew W. Koren
Attorney, Agent, or Firm—Cushman, Darby & Cushman

[57] ABSTRACT

An electro-optical liquid detector assembly comprises a transparent substrate attached at its front surface to a portion of the interior surface of a wind-shield where the exterior surface of the wind-shield is wiped by a wiper blade, a light emission element assembled within the substrate to emit luminous rays towards the wind-shield thereby to cause internal reflection of the luminous rays between the interior and exterior surfaces of the wind-shield, a light receiving element assembled within the substrate to receive the incident luminous rays reflected by the exterior surface of the wind-shield and to produce an electric signal indicative of an amount of the incident luminous rays, a transparent resilient sheet member interposed between the interior surface of the wind-shield and the front surface of the substrate, and a hoder fixedly mounted on a stationary member adjacent the periphery of the interior surface of the wind-shield to support the substrate thereon and press it towards the interior surface of the wind-shield through the resilient sheet member.

6 Claims, 1 Drawing Figure

U.S. Patent    May 20, 1986    4,589,771
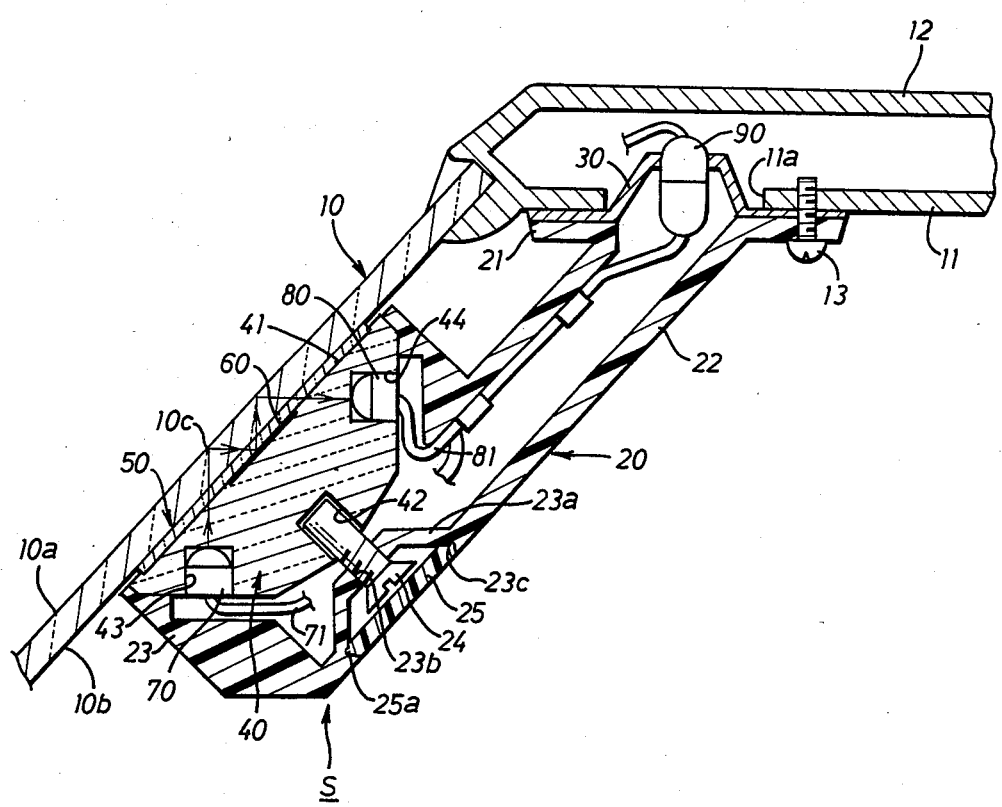

ELECTRO-OPTICAL LIQUID DETECTOR ASEMBLY

BACKGROUND OF THE INVENTION

The present invention relates to an automatic control apparatus for wind-shield wipers, and more particularly to an electro-optical liquid detector assembly for the automatic control apparatus which is adapted to electro-optically detect an adherence condition of liquid such as raindrops on the exterior surface of a wind-shield of wheeled vehicles, airplanes, ships or the like so as to produce an electric control signal necessary for automatic control of a wind-shield wiper in dependence upon a result of the detection.

In general, a conventional electro-optical liquid detector assembly of this kind comprises a transparent substrate attached to a portion of the interior surface of a wind-shield where the exterior surface of the wind-shield is wiped by a wiper blade, a light emission element assembled within the substrate to emit luminous rays towards the wind-shield so as to cause multiple internal reflection of luminous rays in the wind-shield, a light receiving element assembled within the substrate to receive and detect the incident luminous rays reflected by the exterior surface of the wind-shield, and an electric control circuit connected to the light receiving element for producing an electric control signal in dependence upon an amount of the incident luminous rays detected by the light receiving element.

In mounting process of the liquid detector assembly on the interior surface of the wind-shield, a transparent liquid adhesive is utilized to adhere the substrate to the interior surface of the wind-shield and retain it in place. If a portion of the adhesive protrudes from the adherence surface of the substrate during the mounting process, the protruded adhesive has to be wiped away. Additionally, the substrate has to be held in place for a period of time until the adhesive coagulates, resulting in decrease of the working efficiency in the mounting process. If air bubbles are included in the coagulated adhesive, the luminous rays to and from the wind-shield will be diffused due to presence of the air bubbles, resulting in an error in detection of the luminous rays.

SUMMARY OF THE INVENTION

It is, therefore, a primary object of the present invention to provide an electro-optical liquid detector assembly which is fixedly mounted on a portion of the interior surface of a wind-shield in a simple construction without using any adhesive thereby to solve the problems described above.

Another object of the present invention is to provide an improved electro-optical liquid detector assembly the component parts of which can be assembled in place and removed in a simple manner without causing any damage of the interior surface of the wind-shield.

A further object of the present invention is to provide an improved electro-optical liquid detector assembly in which the substrate is resiliently supported in place to protect the optical elements in the detector assembly.

According to the present invention there is provided an improved electro-optical liquid detector assembly which comprises a transparent substrate having a front surface attached to a portion of the interior surface of a wind-shield where the exterior surface of the wind-shield is wiped by a wiper blade, a light emission element assembled within the substrate to emit luminous rays towards the wind-shield so as to cause internal reflection of the luminous rays between the interior and exterior surfaces of the wind-shield, a light receiving element assembled within the substrate to receive the incident luminous rays reflected by the exterior surface of the wind-shield so as to produce an electric signal indicative of an amount of the incident luminous rays, a transparent resilient plate interposed between the interior surface of the wind-shield and the front surface of the substrate, a holder fixedly mounted on a stationary member adjacent the outer circumference of the interior surface of the wind-shield to support the substrate thereon and push it towards the interior surface of the wind-shield through the resilient plate, and means responsive to the electric signal from the light receiving element for producing an electric control signal in dependence upon a value of the electric signal, whereby the resilient plate is uniformly pressed in contact with the interior surface of the wind-shield and the front surface of the substrate.

BRIEF DESCRIPTION OF THE DRAWING

Additional objects and advantages of the present invention will be readily apparent from the following detailed description of a preferred embodiment thereof when taken together with the accompanying single drawing.

DETAILED DESCRIPTION OF THE PREFERRED EMBODIMENT

In the drawing, there is illustrated an electro-optical liquid detector assembly S in accordance with the present invention which is attached to the interior surface of a wind-shield adjacent an inside roof panel 11 of a vehicle compartment. The liquid detector assembly S comprises a holder 20 made of synthetic resin which is secured at its annular flange 21 to a front end portion of inside roof panel 11 through an annular flange of a support member 30 by means of a plurality of fastening screws 13 threaded into the roof panel 11. The holder 20 has a cylindrical arm 22 extending downwardly from the annular flange 21 and arranged in parallel with the wind-shield in the form of a front glass 10. The cylindrical arm 22 is integrally formed at its lower end with a hollow support portion 23 which opens toward a portion of front glass 10 to be wiped by a wiper blade of a wind-shield wiper assembly for the vehicle. The hollow support portion 23 is formed with a central recessed wall 23a into which an adjusting screw 24 is threaded. The adjusting screw 24 is covered by a cover member 25 which is removably coupled at its outer peripheral projection 25a with an annular groove 23c in recessed wall 23a.

Assembled within a cavity of the hollow support portion 23 is a transparent substrate 40 made of transparent synthetic resin such as transparent acrylate resin, poly-carbonate, glass or the like which has substantially the same refractive index as that of the front glass 10 to near infrared rays. In such an arrangement, the holder 20 is fixedly mounted on the inside roof panel 11 in such a manner that the transparent substrate 40 is pressed by resiliency of the holder 20 towards the interior surface of the front glass 10. The transparent substrate 40 is further pressed towards the interior surface 10b of front glass 10 through a transparent resilient plate 50 by means of the adjusting screw 24. The front surface 41 of transparent substrate 40 faces a portion of the exterior surface 10a of glass 10 which is wiped by the wiper blade, and the transparent substrate 40 is firmly retained in place under pressure applied thereto from the screw 24. The substrate 40 is provided at its rear portion with a bore 42 in which the adjusting screw 24 is inserted. The transparent resilient plate 50 is made of transparent silicon rubber the hardness of which is 20–40HS and the thickness of which is 1–3 mm. Under adjustment of the screw 24, the front and rear surfaces of transparent resilient plate 50 are uniformly adhered to the interior surface 10b of front glass 10 and the front surface 41 of substrate 40 respectively without forming any gaps. The transparent resilient plate 50 has substantially the same refractive index as that of front glass 10 to near infrared rays.

A reflection thin plate 60 is adhered by vapour coating to the central portion of the front surface 41 of substrate 40, which thin plate 60 is attached to the rear surface of transparent resilient plate 50 to effect total reflection of the near infrared rays in the front glass 10. The substrate 40 is further provided with a pair of bores 43 and 44 which are arranged symmetrically with respect to the reflection thin plate 60. A light emission element 70 is fixedly contained within the bore 43, while a light receiving element 80 is fixedly contained within the bore 44.

In such an arrangement as described above, the light emission axis of element 70 is located perpendicularly to the bottom surface of bore 43 so that an angle of the light emission axis of element 70 to a normal at an intersect point 10c on the exterior surface 10a of front glass 10 is determined to be a value between critical angles respectively in relation to the outside air on the exterior surface of front glass 10 and in relation to an amount of liquid such as rain drops on the exterior surface of front glass 10. This means that when any liquid does not exist on the exterior surface 10a of front glass 10, the near infrared rays emitted from element 70 along its light emission axis propagate into the front glass 10 through a portion of substrate 40 and are totally reflected by the exterior surface 10a of glass 10 and that when an amount of liquid exists on the exterior surface 10a of front glass 10 at the intersect point 10c, the reflection value of the near infrared rays will decrease. Meanwhile, the light receiving axis of element 80 is located perpendicularly to the bottom surface of bore 44 so that the element 80 receives along its light receiving axis the incident near infrared rays entering into the substrate 40 through transparent resilient plate 50 after multiple internal reflection between the exterior surface 10a of front glass 10 and the reflection thin plate 60.

The light emission element 70 includes therein a light emission diode for emitting the near infrared rays, while the light receiving element 80 includes therein a photodiode for receiving the near infrared rays. The diodes are respectively connected at their input terminals to a connector 90 through leading wires 71 and 81. The connector 90 is mounted on the support member 30 and connected to an electric control circuit (not shown) through a leading wire extending between the inside and outside roof panels 11 and 12. When received an input drive pulse from the electric control circuit through the connector 90 and leading wire 81, the light emission diode of element 70 is energized to emit near infrared rays in the form of a beam along its light emission axis. When received the totally reflected rays, the photodiode of element 80 is energized to produce an electric signal indicative of an amount of the reflected incident rays. Thus, the electric signal is applied to the electric control circuit through the leading wire 81 and connector 90 to produce an electric control signal necessary for automatic control of the wind-shield wiper.

During mounting process of the liquid detector assembly S on the front glass 10, the connector 90 is mounted on the support member 30, the optical elements 70 and 80 are assembled within the respective bores 43 and 44 of substrate 40, and in turn, the substrate 40 is coupled within the hollow support portion 23 of holder 20. Thereafter, the support member 30 is attached to the inside roof panel 11 and received at its annular flange by the flange portion 21 of holer 20. Under such assembling condition, the substrate 40 in holder 20 is pushed towards the interior surface 10b of front glass 10 through the transparent resilient plate 50, and the holder 20 is fixed in place to the inside roof panel 11 by means of fastening screws 13 threaded into the inside roof panel 11 through the respective flanges of holer 20 and support member 30. Subsequently, the adjusting screw 24 is fastened to press the substrate 40 towards the interior surface 10b of front glass 10 through the resilient plate 50 and fixedly retain it in place. Thus, the front and rear surfaces of resilient plate 50 are uniformly pressed in contact with the interior surface 10b of front glass 10 and the front surface 41 of substrate 40 without causing any air gaps. Owing to such uniform contact of the resilient plate 50 with the interior surface 10b of front glass 10 and the front surface 41 of substrate 40, rectilinear propagation of the near infrared rays to and from the exterior surface 10a of front glass 10 is reliably maintained to ensure the function of the liquid detector S.

After attachment of the holder 20, the cover member 25 is coupled with the recessed wall 23a of support portion 23 to cover the head of adjusting screw 24. Thus, the liquid detector assembly S is mounted in place without causing any spoil of the beauty in the vehicle compartment. For repair of the optical elements 70, 80, the substrate 40 and resilient plate 50 can be removed in a simple manner only by removal of the fastening screws 13 without causing any damage of the interior surface 10b of front glass 10. This is useful to facilitate maintenance of the liquid detector assembly S.

In the actual practices of the present invention, the holder 20 may be replaced with a holder made of aluminum in which the substrate 40 is uniformly pressed in contact with the interior surface 10b of front glass 10 through the resilient plate 50 only by fastening of the screws 13. In such a case, the mounting angle of the holder is determined to ensure uniform contact of the resilient plate 50 with the interior surface 10b of front glass 10 and the front surface 41 of substrate 40. As a result, the adjusting screw 24 may be eliminated. Although in the above-described embodiment, the liquid detector assembly S has been attached to an upper peripheral portion of the front glass 10 at a front portion of the inside roof panel 11, it may be attached to a lower peripheral portion of the front glass 10 adjacent a dash board in the vehicle compartment. The liquid detector assembly S may be adapted to a rear glass of the vehicle compartment and also may be adapted to a wind-shield of airplanes, ships or the like. Additionally, the light emission element 70 may be modified to emit visible rays. In such a case, the light receiving element 80 and its related elements are arranged to detect the visible rays reflected by the exterior surface 10a of front glass 10.

As many possible embodiments may be made of the invention without departing from the scope thereof, it is to be understood that all matter herein set forth or shown in the accompanying drawings is to be interpreted as illustrative and not in a limiting sense.

What is claimed is:

1. An electro-optical liquid detector assembly comprising:
   a transparent substrate having a front surface attached to a portion of the interior surface of a wind-shield where the exterior surface of said wind-shield is wiped by a wiper blade;
   a light emission element assembled within said substrate to emit luminous rays towards said wind-shield so as to cause internal reflection of the luminous rays between the interior and exterior surfaces of said wind-shield;
   a light receiving element assembled within said substrate to receive the incident luminous rays reflected by the exterior surface of said wind-shield so as to produce an electric signal indicative of an amount of the incident luminous rays; and
   a transparent resilient plate interposed between the interior surface of said wind-shield and the front surface of said substrate;
   a holder fixedly mounted on a stationary member adjacent the outer circumference of the interior surface of said wind-shield to support said substrate thereon and push it towards the interior surface of said wind-shield through said resilient plate; and
   means responsive to the electric signal from said light receiving element for producing an electric control signal in dependence upon a value of the electric signal.

2. An electro-optical liquid detector assembly according to claim 1, wherein an adjusting screw is threaded into a portion of said holder to press said substrate towards the interior surface of said wind-shield through said transparent resilient plate.

3. An electro-optical liquid detector assembly according to claim 1, wherein a reflection thin plate is adhered to the front surface of said substrate and attached to said transparent resilient plate to effect total reflection of the luminous rays in said wind-shield.

4. An electro-optical liquid detector assembly according to claim 3, wherein said substrate is provided with a pair of bores which are arranged symmetrically with respect to said reflection thin plate, and wherein said light emission element is fixedly contained within one of said bores, and said light receiving element is fixedly contained within the other bore.

5. An electro-optical liquid detector assembly according to claim 1, wherein said substrate is made of transparent synthetic resin, and said resilient plate is made of transparent silicone rubber.

6. An electro-optical liquid detector assembly according to claim 1, wherein said holder is made of synthetic resin which is fixedly mounted on said stationary member in such a manner that said substrate is pressed by resiliency of said holder towards the interior surface of said wind-shield.

* * * * *